(12) United States Patent
Sellstedt et al.

(10) Patent No.: US 7,598,422 B2
(45) Date of Patent: Oct. 6, 2009

(54) PRODUCTION OF CHIRALLY PURE AMINO ALCOHOL INTERMEDIATES, DERIVATIVES THEREOF, AND USES THEREOF

(75) Inventors: John Sellstedt, Eden Prairie, MN (US); Gloria Cheal, Beaconsfield (CA); Razzak Noureldin, Brossard (CA); Anita Wai-Yin Chan, Fort Lee, NJ (US); Panolil Raveendranath, Monroe, NY (US); Thomas Joseph Caggiano, Morrisville, PA (US)

(73) Assignee: Wyeth, Madison, NJ (US)

( * ) Notice: Subject to any disclaimer, the term of this patent is extended or adjusted under 35 U.S.C. 154(b) by 134 days.

(21) Appl. No.: 11/787,962

(22) Filed: Apr. 18, 2007

(65) Prior Publication Data

US 2007/0249869 A1 Oct. 25, 2007

Related U.S. Application Data

(60) Provisional application No. 60/793,896, filed on Apr. 21, 2006.

(51) Int. Cl.
*C07C 209/42* (2006.01)
*C07C 215/08* (2006.01)
*C07D 333/28* (2006.01)

(52) U.S. Cl. ............... 564/489; 564/503; 549/65

(58) Field of Classification Search ............... None
See application file for complete search history.

(56) References Cited

U.S. PATENT DOCUMENTS

| | | | |
|---|---|---|---|
| 6,610,734 | B2 | 8/2003 | Kreft et al. |
| 6,657,070 | B2 | 12/2003 | Resnick |
| 6,800,764 | B2 | 10/2004 | Kreft et al. |
| 6,878,742 | B2 | 4/2005 | Kreft et al. |
| 7,166,622 | B2 | 1/2007 | Kreft et al. |
| 2004/0198778 | A1 | 10/2004 | Kreft et al. |
| 2005/0171180 | A1 | 8/2005 | Resnick et al. |
| 2005/0196813 | A1 | 9/2005 | Kreft et al. |
| 2007/0037778 | A1 | 2/2007 | Kreft et al. |

FOREIGN PATENT DOCUMENTS

| | | |
|---|---|---|
| WO | WO 03/050062 A2 | 6/2003 |
| WO | WO 03/050063 A3 | 6/2003 |
| WO | WO 03/103660 A1 | 12/2003 |
| WO | WO 2004/092155 A1 | 10/2004 |
| WO | WO 2005/073198 A1 | 8/2005 |

OTHER PUBLICATIONS

Evans et al, Electrophilic Azide Transfer to Chiral Enolates. A General Approach to the Asymmetric Synthesis of α-Amono Acids, J. Am. Chem. Soc., 109:6881-6883, (1987).

Testa et al, Prodrugs Revisited: The "Ad Hoc" Approach as a Complement to Ligand Design, Medicinal Research Reviews, vol. 16, No. 3, pp. 233-241, (1996).

Evans et al, The Asymmetric Synthesis of α-Amino and α-Hydrazino Acid Derivatives via the Stereoselective Amination of Chiral Enolates with Azodiacarboxylate Esters, Tetrahedron, vol. 44, No. 17, pp. 5525-5540, (1988).

Green, Protective Groups in Organic Synthesis, $2^{nd}$ Edition, pp. 349-362, (1991).

Wuts, P. W., Vogel's Textbook of Practical Organic Chemistry, VII, 6, p. 1129, (1978).

*Primary Examiner*—Brian J Davis
(74) *Attorney, Agent, or Firm*—Scott K. Larsen; Howson & Howson LLP

(57) ABSTRACT

A method of selectively preparing a chiral 2S-amino alcohol useful in preparation of an amide sulfonated or acylated with alkyl, substituted aryl or substituted heteroaryl is described. The method involves reacting a di-tert-butyl diazene-1,2-dicarboxylate with a (4S)-4-benzyl-3-[(S)-trifluoromethyl-alkyl substituted alkanoyl]-1,3-oxazolidin-2-one to afford a di-tert-butyl 1-(1S,2S)-([(4S)-4-benzyl-2-oxo-1,3-oxazolidine-3-yl]-carbonyl}-trifluoromethyl-alkyl substituted alkyl) hydrazine-1,2-dicarboxylate. This dicarboxylate is then reduced to yield di-tert-butyl 1-(1S,2S)-[trifluoromethyl-alkyl substituted alkyl]hydrazine-1-(hydroxymethyl)-1,2-dicarboxylate. The resulting product is deblocked with an acid to yield the acid addition salt of (2S,3S)-trifluoro-hydrazino-methyl alkan-1-ol. The acid addition salt of (2S,3S)-trifluor-2-hydrazino-methyl alkan-1-ol is hydrogenated in the presence of a suitable metal catalyst to yield the amino alcohol (2S,3S)-2-amino-trifluoro-methyl alkan-1-ol HCl.

20 Claims, No Drawings

PRODUCTION OF CHIRALLY PURE AMINO ALCOHOL INTERMEDIATES, DERIVATIVES THEREOF, AND USES THEREOF

CROSS-REFERENCE TO RELATED APPLICATION

This application claims the benefit under 35 USC 119(e) of U.S. Provisional Patent Application No. 60/793,896, filed Apr. 21, 2006.

BACKGROUND OF THE INVENTION

Alzheimer's Disease (AD) is the most common form of dementia (loss of memory) in the elderly. The main pathological lesions of AD found in the brain consist of extracellular deposits of beta amyloid protein in the form of plaques and angiopathy and intracellular neurofibrillary tangles of aggregated hyperphosphorylated tau protein. Recent evidence has revealed that elevated beta amyloid levels in brain not only precede tau pathology but also correlate with cognitive decline. Further suggesting a causative role for beta amyloid in AD, recent studies have shown that aggregated beta amyloid is toxic to neurons in cell culture and has a detrimental effect on memory. This suggests that reducing beta amyloid levels is a viable therapeutic strategy for the treatment of AD.

Beta amyloid protein is composed mainly of 39-42 amino acid peptides and is produced from a larger precursor protein called amyloid precursor protein (APP) by the sequential action of the proteases beta and gamma secretase. Although rare, cases of early onset AD have been attributed to genetic mutations in APP that lead to an overproduction of either total beta amyloid protein or its more aggregation-prone 42 amino acid isoform. Furthermore, people with Down's Syndrome possess an extra chromosome that contains the gene that encodes APP and thus have elevated beta amyloid levels and invariably develop AD later in life.

Methods of producing substituted heteroaryl sulfonamide compounds useful as beta amyloid inhibitors have been described [U.S. Pat. Nos. 6,610,734; 6,878,742]. These methods have included the construction of an acylated Evans oxazolidone chiral auxiliary, which is then converted to the corresponding enolate and electrophilically aminated with trisyl azide to afford the desired, key intermediate (*J. Am. Chem. Soc.* 109: 6881-6883 (1987)). The azide intermediate is then hydrolyzed to the α-azido acid and reduced to the chirally pure α-amino acid which can be converted to the corresponding N-sulfonyl 2-amino alcohols. However, this method utilizes reagents, notably, the trisyl azide, which are not suitable for large scale production.

What are needed are improved methods of making compounds that are effective in lowering beta amyloid production.

SUMMARY OF THE INVENTION

In one aspect, the invention provides a method of producing a 1S,2S-amino alcohol having two chiral centers, which is useful in production of a number of target compounds. The method of the invention avoids reagents that cannot be used for scale-up and allows the preparation of the target compounds without chromatography and excellent chiral purity, chemical purity and stability.

The invention further provides a method for stereoselectively introducing an S-nitrogen in a chiral 2S-amino alcohol in order to prepare target compounds having a 1S,2S configuration.

Other aspects and advantages of the invention will be apparent from the following detailed description of the invention.

DETAILED DESCRIPTION OF THE INVENTION

The invention provides methods of producing a 1S,2S amino alcohol, or salt thereof, having at least one chiral centers from the amino alcohol is sulfonylated or acylated with residues containing an alkyl, substituted aryl or substituted heteroaryl group.

Amino alcohols having two chiral centers, salts and derivatives, and intermediates thereof, may be prepared according to the present invention. Typically, the 2S-amino alcohols are characterized by the formula:

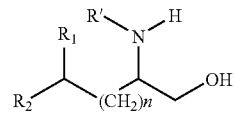

Suitably, in the above formulae, n is 0 to about 10; $R_1$ and $R_2$ are independently selected from the group consisting of lower alkyl, substituted lower alkyl, lower alkenyl, $CF_3$, cycloalkyl, substituted cycloalkyl, phenyl, substituted phenyl, benzyl, substituted benzyl, $CH_2$cycloalkyl, $CH_2$-3-indole, CH(loweralkyl)-2-furan, CH(loweralkyl)-4-methoxyphenyl, CH(loweralkyl)phenyl, or CH(OH)-4-$SCH_3$-phenyl; and R' is selected from among H, lower alkyl, substituted lower alkyl, lower alkenyl, $CF_3$, heterocycle, substituted heterocycle, phenyl, substituted phenyl, benzyl, substituted benzyl, cycloalkyl, and substituted cycloalkyl, among other suitable groups. In one embodiment, the substituted lower alkyl is a fluoroalkyl. These compounds may be readily converted to desired compounds including, without limitation, the corresponding aldehydes, oximes, and pharmaceutically acceptable salts, hydrates, and prodrugs thereof. However, the compounds produced by the methods of the present invention are not limited by the above formulae.

As used herein, the term "chirally pure" refers to compounds which are in about 100% S-(or R) enantiomeric form as measured by chiral high performance liquid chromatography (HPLC). Although many of the examples provided herein illustrate formation of the S-enantiomer, the present invention can give the R enantiomer if the auxiliary is changed. Other methods of measuring chiral purity include conventional analytical methods, including specific rotation, and conventional chemical methods. However, the technique used to measure chiral purity is not a limitation on the present invention.

As used herein, the term "pharmaceutically useful" refers to compounds having a desired biological effect, whether as a therapeutic, immune stimulant or suppressant, adjuvant, or vaccinal agent. Similarly, a variety of compounds which are suitable for use in non-pharmaceutical applications, e.g., a diagnostic, a marker, among others may be produced by the method of the invention. However, other pharmaceutically useful compounds may be produced by this method.

The compounds produced by the present invention and any target compounds into which they are converted can be used in the form of salts derived from pharmaceutically or physiologically acceptable acids or bases. Other salts include salts with alkali metals or alkaline earth metals, such as sodium (e.g., sodium hydroxide), potassium (e.g., potassium hydroxide), calcium or magnesium.

These salts, as well as other compounds produced by the method of the invention may be in the form of esters, carbamates and other conventional "pro-drug" forms, which, when administered in such form, convert to the active moiety in vivo. In one desirable embodiment, the prodrugs are esters. See, e.g., B. Testa and J. Caldwell, "Prodrugs Revisited: The "Ad Hoc" Approach as a Complement to Ligand Design", Medicinal Research Reviews, 16(3):233-241, ed., John Wiley & Sons (1996).

The term "alkyl" is used herein to refer to both straight- and branched-chain saturated aliphatic hydrocarbon groups having one to ten carbon atoms, preferably one to eight carbon atoms and, most preferably, one to six carbon atoms; as used herein, the term "lower alkyl" refers to straight- and branched-chain saturated aliphatic hydrocarbon groups having one to six carbon atoms;

The terms "substituted alkyl", as just described having from one to three substituents selected from the group including halogen, CN, OH, $NO_2$, amino, aryl, heterocyclic, substituted aryl, substituted heterocyclic, alkoxy, substituted alkoxy, aryloxy, substituted alkyloxy, alkylcarbonyl, alkylcarboxy, alkylamino, and arylthio. These substituents may be attached to any carbon of an alkyl, alkenyl, or alkynyl group provided that the attachment constitutes a stable chemical moiety.

As used herein, a fluoroalkyl is a substituted alkyl, which is substituted with one to three fluorine atoms. As used herein, trifluoromethyl, i.e., $CF_3$, refers to a fluoroalkyl having one carbon atom, which carbon atom is the point of attachment.

The term "aryl" is used herein to refer to a carbocyclic aromatic system, which may be a single ring, or multiple aromatic rings fused or linked together as such that at least one part of the fused or linked rings forms the conjugated aromatic system. The aryl groups include, but are not limited to, phenyl, naphthyl, biphenyl, anthryl, tetrahydronaphthyl, phenanthryl, and indane.

The term "substituted aryl" refers to aryl as just defined having one to four substituents from the group including halogen, CN, OH, $NO_2$, amino, alkyl, cycloalkyl, alkoxy, aryloxy, substituted alkyloxy, alkylcarbonyl, alkylcarboxy, alkylamino, and arylthio.

The term "substituted benzyl" refers to a benzyl (Bn) group, having substituted on the benzene ring, one to five substituents from the group including halogen, CN, OH, $NO_2$, amino, alkyl, cycloalkyl, alkoxy, aryloxy, substituted alkyloxy, alkylcarbonyl, alkylcarboxy, alkylamino, and arylthio.

The term "heterocyclic" is used herein to describe a stable 4- to 7-membered monocyclic or a stable multicyclic heterocyclic ring which is saturated, partially unsaturated, or unsaturated, and which consists of carbon atoms and from one to four heteroatoms selected from the group including N, O, and S atoms. The N and S atoms may be oxidized. The heterocyclic ring also includes any multicyclic ring in which any of above defined heterocyclic rings is fused to an aryl ring. The heterocyclic ring may be attached at any heteroatom or carbon atom provided the resultant structure is chemically stable. Such heterocyclic groups include, for example, tetrahydrofuran, piperidinyl, piperazinyl, 2-oxopiperidinyl, azepinyl, pyrrolidinyl, imidazolyl, pyridyl, pyrazinyl, pyrimidinyl, pyridazinyl, oxazolyl, isoxazolyl, morpholinyl, indolyl, quinolinyl, thienyl, furyl, benzofuranyl, benzothienyl, thiamorpholinyl, thiamorpholinyl sulfoxide, isoquinolinyl, and tetrahydrothiopyran.

The term "substituted heterocyclic" is used herein to describe the heterocyclic just defined having one to four substituents selected from the group which includes halogen, CN, OH, $NO_2$, amino, alkyl, substituted alkyl, cycloalkyl, substituted cycloalkyl, alkoxy, substituted alkoxy, aryloxy, substituted aryloxy, alkyloxy, substituted alkyloxy, alkylcarbonyl, substituted alkylcarbonyl, alkylcarboxy, substituted alkylcarboxy, alkylamino, substituted alkylamino, arylthio, or substituted arylthio.

The term "substituted cycloalkyl" is used herein to describe a carbon-based ring having more than 3 carbon-atoms which forms a stable ring and having from one to five substituents selected from the group consisting of halogen, CN, OH, $NO_2$, amino, alkyl, substituted alkyl, alkoxy, aryloxy, substituted alkyloxy, alkylcarbonyl, alkylcarboxy, alkylamino, substituted alkylamino, arylthio, heterocyclic, substituted heterocyclic, aminoalkyl, and substituted aminoalkyl.

The term "alkoxy" is used herein to refer to the O(alkyl) group, where the point of attachment is through the oxygen-atom and the alkyl can be optionally substituted. The term "aryloxy" is used herein to refer to the O(aryl) group, where the point of attachment is through the oxygen-atom and the aryl can be optionally substituted. The term "alkylcarbonyl" is used herein to refer to the CO(alkyl) group, where the alkyl can be optionally substituted and the point of attachment is through the carbon atom of the carbonyl group. The term "alkylcarboxy" is used herein to refer to the COO(alkyl) group, where the alkyl can be optionally substituted and the point of attachment is through the carbon atom of the carboxy group. The term "aminoalkyl" refers to both secondary and tertiary amines wherein the alkyl or substituted alkyl groups, containing one to eight carbon atoms, which may be either same or different, and the point of attachment is on the nitrogen atom.

The term "halogen" refers to Cl, Br, F, or I.

The term "strong non-nucleophilic base" refers to a basic reagent, which does not act as a nucleophile towards the reactants utilized in the reaction. A number of non-nucleophilic bases are known in the art and include sodium hydride, potassium hydride, lithium diisopropylamide and potassium hexamethyldisilazide.

The term "aqueous base" refers to a solution composed of, at a minimum, a base and water. A number of bases which readily dissolve in water are known in the art and include alkali metal hydroxides such as lithium hydroxide, sodium hydroxide or potassium hydroxide, among others. The aqueous base solution may further contain other reagents which do not interfere with the reactions of the present invention, and include organic solvents such as tetrahydrofuran, methanol, ethanol, or hydrocarbon solvents, salts such as sodium chloride, and buffers, among others.

The term "aqueous acid" refers to a solution composed of, at a minimum, an acid and water. The aqueous acid solution may further contain other reagents which do not interfere with the reactions of the present invention.

The term "strong acid" or "strong base" refers to an acid or base that is highly ionized in solution. Common strong acids include HCl, HBr, HI, HNO3, $H_2SO_4$, and $HClO_4$. Common strong bases include hydroxides of the alkali metals (Li, Na, K, Cs) and hydroxides of the heavy alkaline earths (Ca, Sr, Ba).

The term "inorganic" acid or "inorganic" base includes acids and bases which do not contain carbon.

The term "organic solvent" may include any carbon-containing solvent known in the art, which does not react with the reagents utilized in the reaction and includes saturated hydrocarbon solvents, unsaturated hydrocarbon solvents, including aromatic hydrocarbon solvents, alcohols, halocarbons, ethers, and acetates, among others.

Synthesis

The synthetic methods of the invention are described in the following scheme. These methods, together with synthetic methods known in the synthetic organic arts or variations of these methods by one skilled in the art are used in the present invention. See, generally, *Comprehensive Organic Synthesis*, "Selectivity, Strategy & Efficiency in Modern Organic Chemistry", ed., I. Fleming, Pergamon Press, New York (1991); *Comprehensive Organic Chemistry*, "The Synthesis and Reactions of Organic Compounds", ed. J. F. Stoddard, Pergamon Press, New York (1979)). In the following scheme, the term "BOC" refers to a t-butyl oxy carbonyl group.

Scheme I

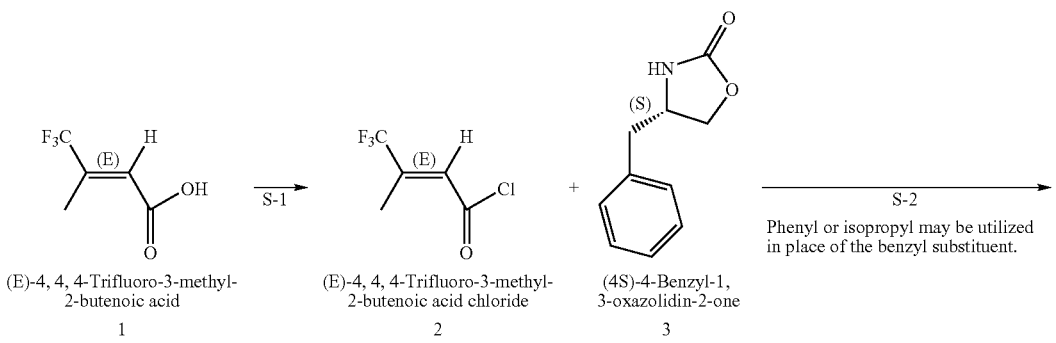

(E)-4, 4, 4-Trifluoro-3-methyl-2-butenoic acid
1

(E)-4, 4, 4-Trifluoro-3-methyl-2-butenoic acid chloride
2

(4S)-4-Benzyl-1, 3-oxazolidin-2-one
3

Phenyl or isopropyl may be utilized in place of the benzyl substituent.

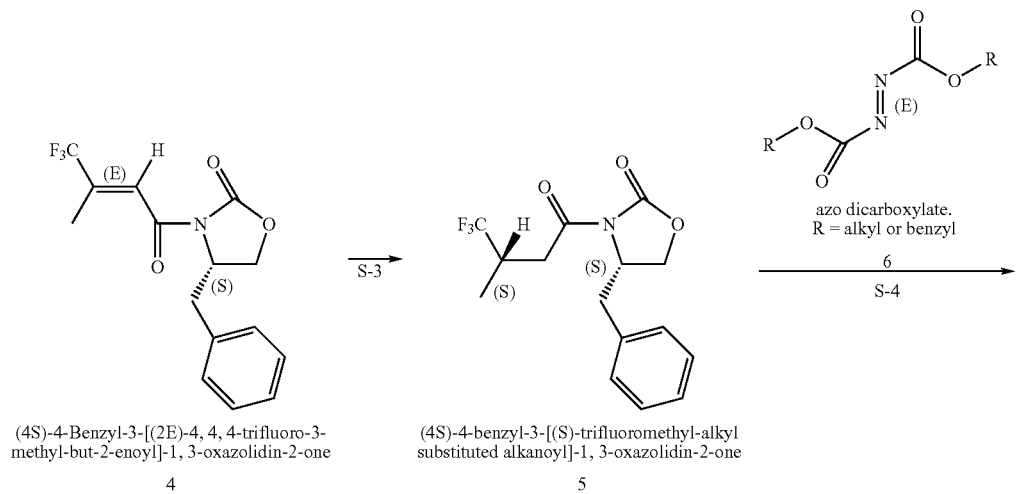

(4S)-4-Benzyl-3-[(2E)-4, 4, 4-trifluoro-3-methyl-but-2-enoyl]-1, 3-oxazolidin-2-one
4

(4S)-4-benzyl-3-[(S)-trifluoromethyl-alkyl substituted alkanoyl]-1, 3-oxazolidin-2-one
5 azo dicarboxylate.
R = alkyl or benzyl
6

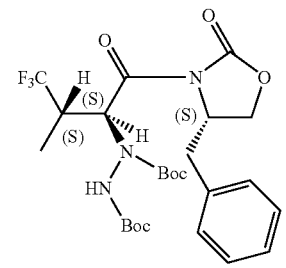

di-tert-butyl 1-(1S, 2S)-([(4S)-4-benzyl-2-oxo-1, 3-oxazolidine-3-yl]-carbonyl]-trifluoromethyl-alkyl substituted alkyl)hydrazine-1, 2-dicarboxylate
7

S-5

-continued

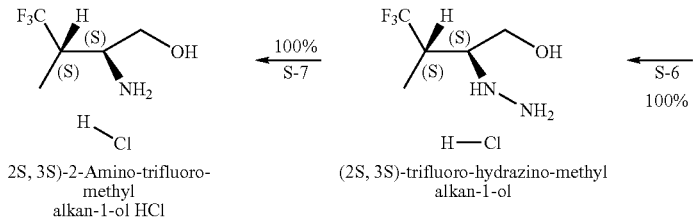

2S, 3S)-2-Amino-trifluoro-
methyl
alkan-1-ol HCl

9

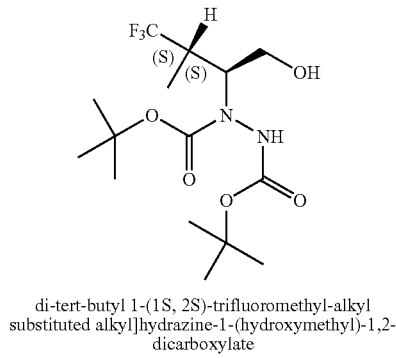

di-tert-butyl 1-(1S, 2S)-trifluoromethyl-alkyl
substituted alkyl]hydrazine-1-(hydroxymethyl)-1,2-
dicarboxylate

8

The acid in the starting material is activated. As illustrated, an acyl halide is prepared. Alternative methods, e.g., preparation of a mixed anhydride, may be utilized. As illustrated in Scheme I, a dialkyl azodicarboxylate is reacted at the carbanion at the 2 position under cold conditions with a (4S)-4-benzyl-3-[(S)-trifluoromethyl-alkyl substituted alkanoyl]-1, 3-oxazolidin-2-one which has been dissolved in lithium diisopropyl amide (LDA) or potassium bis(trimethyl)silylamide, and a suitable solvent system (e.g., tetrahydrofuran, THF). This approach was reported by the Evans group (Tetrahedron 44, (1988), 5525, JACS, 104, (1982), 1734). In the example provided herein, di-tert-butyl azodicarboxylate in used for ease of removal in a suitable reaction. In another embodiment the substituent may be dibenzyl, bis(2-trichloroethyl), dialkyl or diaryl or another suitable group selected by one of skill in the art. Similarly, in the example provided herein, a 4(S)-benzyl oxazolidinone is used as the chiral auxiliary, however, other 4- and 3,4 disubstituted chiral oxazolidines (e.g., (4S)-4-phenyloxazolidinone) known to one skilled in the art may be used.

In one embodiment, the solvent system for the LDA comprises tetrahydrofuran (THF). The solvent may also contain other solvents including, e.g., heptane, ethylbenzene, or mixtures thereof. Typically, THF is the primary component of the solvent system. The reaction of the di-tert-butyl diazene-1,2-dicarboxylate with the anion formed from the acylated oxazolidinone may be quenched with glacial acetic acid. The THF is removed by distillation and replacement with toluene, separation of the layers and washing twice with saturated NaHCO$_3$ and water provides a toluene solution. The toluene is removed by vacuum distillation. The resulting product is a di-tert-butyl 1-(1S,2S)-([(4S)-4-benzyl-2-oxo-1,3-oxazolidine-3-yl]-carbonyl}-trifluoromethyl-alkyl substituted alkyl) hydrazine-1,2-dicarboxylate. This methodology can also be applied to nonfluorinated systems.

The resulting di-tert-butyl 1-(1S,2S)-([(4S)-4-benzyl-2-oxo-1,3-oxazolidine-3-yl]-carbonyl}-trifluoromethyl-alkyl substituted alkyl)hydrazine-1,2-dicarboxylate is reduced. The reduction involves reaction of dissolved di-tert-butyl 1-(1S,2S)-(1-{[(4S)-4-benzyl-2-oxo-1,3-oxazolidine-3-yl]-carbonyl}-trifluoromethyl-alkyl substituted alkyl)hydrazine-1,2-dicarboxylate and LiBH$_4$ in tetrahydrofuran and water, or, alternatively, t-butyl methyl ether (TBME) and water. Typically, the reaction is allowed to proceed for at least about 16 hours prior to adding an acid (e.g., HCl) to the reaction mixture. The aqueous phase is separated and the organic phase is washed. The solution is then stripped until a solid is obtained. The solution is cooled, the solid filtered, and washed with acetonitrile. Thereafter, a sample of the solid may be assayed to ensure that the product has a melting point of greater than 181° C.

The resulting di-tert-butyl 1-(1S,2S)-[trifluoromethyl-alkyl substituted alkyl]hydrazine-1-(hydroxymethyl)-1,2-dicarboxylate is deblocked to yield the acid addition salt of (2S,3S)-trifluoro-hydrazino-methyl alkan-1-ol. Deblocking is achieved by mixing the di-tert-butyl 1-(1S,2S)-[trifluoromethyl-alkyl substituted alkyl]hydrazine-1-(hydroxymethyl-1, 2-dicarboxylate with a strong acid, e.g., HCl. Typically, this is performed at a temperature of about 30° C. to 50° C. Alternatively, if the dibenzyl ester is utilized rather than a tert-butyl ester, then other deblocking methods can be used, e.g., O. Pouparbid, C. Greck and J-P, Genet, *Synlett*, 1998, 1279.

The amino alcohol (2S,3S)-2-amino-trifluoromethyl methyl alkan-1-ol HCl is hydrogenated with the acid addition salt of (2S,3S)-trifluor-2-hydrazino-methyl alkan-1-ol in the presence of suitable metal catalyst. Examples of suitable metal catalysts include, e.g., PtO$_2$, Pd, and RaNi. Other catalysts can be readily substituted.

In one embodiment, the method of the invention further comprises the step of triturating the resulting product of in a suitable solvent to remove trapped metal contaminants from the catalyst. This can be accomplished using acetonitrile or 20% (w/w) acetonitrile/EtOAc to remove the amino alcohol-catalyst complex from the primarily insoluble amino alcohol HCl salt.

Advantageously, the method of the invention provides a novel method of constructing an alpha amino acylated Evans oxazolidone, which avoids trisyl azide and other reagents, which are not suitable for large scale production. The resulting product is useful in the synthesis of a variety of pharmaceutically useful target compounds where the amine from the amino alcohol is reacted to form a sulfonamide or acylated with alkyl, substituted aryl or substituted heteroaryl.

The resulting amino alcohol can then be used in the synthesis of a variety of desirable products. For example, the amino alcohol produced according to the method of the invention can be used to produce the substituted aryl or substituted heteroaryl sulfonamide compounds described in Porte et al, U.S. Provisional Patent Application No. 60/793, 852, filed Apr. 21, 2006, filed on the same date herewith, entitled "Trifluoromethyl-Containing Phenylsulfonamide Beta Amyloid Inhibitors", U.S. Pat. Nos. 6,878,742, 6,610, 734, WO 092152A1. Suitable techniques for the acylation reactions described herein may be readily selected by one of skill in the art. See, generally, Vogel's Textbook of Practical Organic Chemistry and Greene, Theodora W.; Wuts, Peter G. M. Protective Groups in Organic Synthesis. 2nd Ed. (1991).

For substituted aryl or heteroaryl sulfonamide compounds such as those described in the exemplary documents described above, the 2S-amino alcohol or the salt thereof may be reacted with a suitable solvent and a tertiary base in the presence of the substituted aryl sulfonyl halide (e.g., sulfonyl chloride) or substituted heteroaryl sulfonyl sulfonate ester (e.g., pentafluorophenylsulfonyl ester).

Examples of suitable solvents include dichloromethane, THF, methyl-tert-butyl ether, and pyridine. Examples of suitable tertiary bases include, e.g., methylmorpholine, pyridines, triethylamine, trimethylamine, ethylmethylpropylamine, DMAP, and disopropyl ethyl amine.

In one embodiment, the invention further comprises the step of protecting the amino alcohol by silylation prior to reacting the amino alcohol with the substituted aryl sulfonyl compound or substituted heteroaryl sulfonyl compound. At the completion of the reaction, the product is deblocked to yield the desired substituted aryl or substituted heteroaryl sulfonamide.

The substituted aryl or substituted heteroaryl sulfonamide compounds prepared using the 1S,2S-amino alcohols of the present invention have utility for the prevention and treatment of disorders involving beta amyloid production including cerebrovascular diseases. The compounds of the present invention have utility for the prevention and treatment of AD by virtue of their ability to reduce beta amyloid production.

The following examples are illustrative of the methods of synthesizing 2S-amino alcohols according to the invention, and methods of synthesizing same. It will be readily understood by one of skill in the art that the specific conditions described herein for producing these compounds can be varied without departing from the scope of the present invention. It will be further understood that other compounds, as well as other salts, hydrates, and/or prodrugs thereof, can be synthesized using the method of the invention.

EXAMPLES

Example 1

Preparation of (2S,3S)-2-Amino-4,4,4-trifluoro-3-methyl-butan-1-ol HCl

A. Preparation of (4S)-4-Benzyl-3-[(2E)-4,4,4-trifluoro-3-methyl-but-2-enoyl]-1,3-oxazolidin-2-one (4S)-4-Benzyl-1,3-oxazolidin-2-one (828 g, 4.67 moles) was dissolved in 6.8 L THF and cool to −40 to −50° C. To the solution of (4S)-4-benzyl-1,3-oxazolidin-2-one, 2.5 M BuLi in hexanes (1302 g, 1880 mL, 4.70 mole, 1.01 equivalents) was added while keeping the temperature at <−40° C. To the cold solution of the Li salt of (4S)-4-benzyl-1,3-oxazolidin-2-one, 4,4,4-trifluoro-3-methyl-2-butenoic acid chloride (887 g, 5.14 moles, 1.1 equivalents) was added over 10-30 minutes, allowing the temperature to rise and wash in with 0.4 L THF. The reaction was warmed to 20-25° C. and stirred for 2 h. 0.9 L water was added and stirred for 16 h. The THF was distilled off with a bath temperature of 35° C. and vacuum <40 mm Hg. Toluene (5.8 L) was added and the phases split. 4-L saturated NaHCO$_3$ was used to wash (2×), the mixture was filtered through Celite and the phases split. 2.5-L water (2×) was used as a wash and the toluene layer was filtered through Celite. The remaining water was removed. The toluene was distilled off with a bath temperature of 40° C. and vacuum <40 mm Hg. At the end of the distillation the product started to crystallize with a pot temperature of 30° C. Distillation is continued to a pot temperature of 35° C. giving a solid mobile mass of 1456 g. The solid is dissolved in 2.9 L (2 vol) EtOH (99.5% EtOH:0.5% toluene). While stirring at 20-25° C., water (1.09 L, 0.75 vol) was added over 1 h forming crystals. Stirring is continued for 16 h at 15-25° C., followed by cooling to 0-5° C. and holding for 1 h. The crystals are filtered, washed with filtrate and dried at 50° C. for 16 h giving 1229 g, 84% of (4S)-4-benzyl-3-[(2E)-4,4,4-trifluoro-3-methyl-but-2-enoyl]-1,3-oxazolidin-2-one.

B. Preparation of (4S)-4-Benzyl-3-[(3S)-4,4,4-trifluoro-3-methylbutanoyl]-1,3-oxazolidin-2-one (4S)-4-Benzyl-3-[(2E)-4,4,4-trifluoro-3-methyl-but-2-enoyl]-1,3-oxazolidin-2-one (4) (1327 g, 4.24 mole) and 50.6 g of 5% Pd/C (50% wet) were added to the hydrogenation vessel and purged with N$_2$ to remove air. 16.8 L of EtOH (99.5% EtOH:0.5% toluene) was cooled to 0 to −5° C., added to the vessel and purged for hydrogenation while holding the temperature at 0 to −5° C. The hydrogenation was started with 20 psig H$_2$ holding the temperature at 0 to −5° C. for 17-34 h until the theoretical amount of H$_2$ was consumed. The mixture was filtered through a 0.2μ filter and the filter was washed with 24 L EtOAc. In order to remove Pd, it was necessary to remove the EtOH, replace it with toluene and filter the toluene solution. The solvent was removed giving a solid that is dissolved in 6 L toluene, followed by stirring for 2 h at 0-5° C. and filtering on a 1 kg Celite pad. Toluene (4 L) was used as a wash. The toluene was removed and 1 L EtOH added, followed by stirring at 10° C. for 2 h. Filtration and washing were with 0.2 L EtOH and 1 L heptane. Product was dried at 35° C. for 15 h giving 810 g 61% yield of 5 with SS to RS ratio of 96:4. The filtrate was concentrated to 412 g of a yellow soft solid.

C. Preparation of di-tert-butyl 1-((1S,2S)-1-{[(4S)-4-benzyl-2-oxo-1,3-oxazolidine-3-yl]-carbonyl}-3,3,3-trifluoro-2-methylpropyl)hydrazine-1,2-dicarboxylate (4S)-4-Benzyl-3-[(3S)-4,4,4-trifluoro-3-methylbutanoyl]-1,3-oxazolidin-2-one (5) (92% ee) (268.4 g, 0.851 mole) was dissolved in 1.8 L THF. The solution was stirred under N$_2$ and cooled to −75° C. At −70 to −76° C. add 2.0 M LDA in heptane/tetrahydrofuran/ethylbenzene (470 mL, 0.940 mole, 1.1 equivalents) over 2 hours. The solution was stirred for 30 minutes at <−70° C. Di-tert-butyl azodicarboxylate (240 g, 1.02 moles, 1.2 equivalents) was dissolved in 900 mL THF and the solution cooled to 0-5° C. A solution of 146 mL of glacial acetic acid was prepared in 200 mL THF. The solution of di-tert-butyl azodicarboxylate was added rapidly as possible maintaining the temperature at <−70° C. This usually takes about 1 hour. After di-tert-butyl azodicarboxylate has been added, stir for 3 minutes and the solution of acetic acid was added as rapidly as possible letting the temperature rise as it is being added. The solution is warmed to room temperature over a period of 2 hours. The flask was prepared for distillation and the THF removed with a jacket temperature of 35° C. at 60-70 mm Hg. 2 L toluene and 1.2 L water were added. The layers were separated and washed with 1 L water, 1 L 0.25 M HCl, twice with 0.5 L saturated NaHCO$_3$ and twice with 0.5 L water. The toluene solution was added to a flask prepared for vacuum distillation with a jacket temperature of 30° C. and 20-1 mm Hg. A quantitative yield of 7 (464 g) as an oil is the usual result.

D. Preparation of di-tert-butyl J-[(1S,2S)-3,3,3-trifluoro-1-(hydroxymethyl)-2-methylpropyl]hydrazine-1,2-dicarboxylate The di-tert-butyl 1-((1S,2S)-1-{[(4S)-4-benzyl-2-oxo-1,3-oxazolidine-3-yl]-carbonyl}-3,3,3-trifluoro-2-methylpropyl)hydrazine-1,2-dicarboxylate oil (464 g, 0.851 mole) from step C was dissolved in 5.8 L of methyl t-butyl ether (TBME)

and 15.3 g water (0.851 mole, 1 equivalent) was added. The solution was cooled to 0-5° C. A solution of $LiBH_4$ (31.37 g, 1.44 mole, 1.7 equivalents) in THF 690 mL was prepared by cooling the THF to 0-10° C. and adding the $LiBH_4$ slowly under $N_2$. The $LiBH_4$ solution was added over 1 hour at 0-5° C. and washed in with 100 mL of TBME. The mixture is stirred for 16 hours warmed to room temperature. 2 L water is added and stirred until gas evolution stops. A 1-L solution of 1 M HCl was prepared and added to the reaction mixture until it reached pH 1-2 (about 850 mL was required). The aqueous phase were separated and the organic phase washed twice with 1 L of water (pH 4 after the second wash), 1 L of saturated $NaHCO_3$ diluted with water 9:1 (pH 9), twice with 0.5 L brine and dried over 300 g MgSO4. The solution was filtered. The solution was stripped until a solid was obtained under high vacuum (<10 mm Hg) giving 420 g. 2.5 volumes (1050 mL) of $CH_3CN$ was added and brought to reflux to dissolve the solid. The solution was cooled to 20-25° C. and stirred for 16 h. The solid was filtered and washed with $CH_3CN$ giving 214.4 g, 68% yield. The m.p. must be >181° C. to assure chiral purity. HPLC was run to make sure no (4S)-4-Benzyl-1,3-oxazolidin-2-one was in the product.

E. Preparation of (2S,3S)-4,4,4-Trifluoro-2-hydrazino-3-methyl-butan-1-ol HCl

Di-tert-butyl 1-[(1S,2S)-3,3,3-trifluoro-1-(hydroxymethyl)-2-methylpropyl]hydrazine-1,2-dicarboxylate (214.4 g, 0.576 mole) was dissolved in 640 mL THF. The solution was warmed to 30° C. and concentrated HCl (240 mL, 2.87 moles, 5 equivalents) was added drop wise over 20 minutes at 30-50° C. The solution was maintained at 50° C. for 2 hours and the THF was removed with aspirator vacuum at 30-60° C. The HCl solution was washed twice with 300 mL TBME. The aqueous phase was then stripped to a white solid using aspirator and vacuum pump at 50-60° C. The resulting solid was dried at 50° C. under vacuum at <10 mm Hg giving 108.3 g, 90% yield of (2S,3S)-4,4,4-Trifluoro-2-hydrazino-3-methyl-butan-1-ol HCl.

F. Preparation of (2S,3S)-2-Amino-4,4,4-trifluoro-3-methyl-butan-1-ol HCl (2S,3S)-4,4,4-Trifluoro-2-hydrazino-3-methyl-butan-1-ol HCl (130 g, 0.623 mole) was dissolved in 1.4 L MeOH with 60 mL concentrated HCl. The solution was hydrogenated with 10 g $PtO_2$ at 50 psig for 12 hours. The mixture was filtered and the filter washed with 1 L MeOH. The MeOH was removed to dryness under vacuum at 30-40° C. The solid was chased with two portions of 1 L MeOH. The solid was stirred with 0.5 L MeOH for 1 hour and the $NH_4Cl$ was removed by filtration. To remove more $NH_4Cl$, the filtrate can be concentrated to 2/3 volume and crystallized $NH_4Cl$ removed by filtration. The filtrate was concentrated to dryness and dried at 35° C. at <10 mm Hg. The hydrochloride can be purified by stirring with 20% v/v $CH_3CN$:EtOAc removing a green coloring and removing essentially all the Pt to the 10 ppm level.

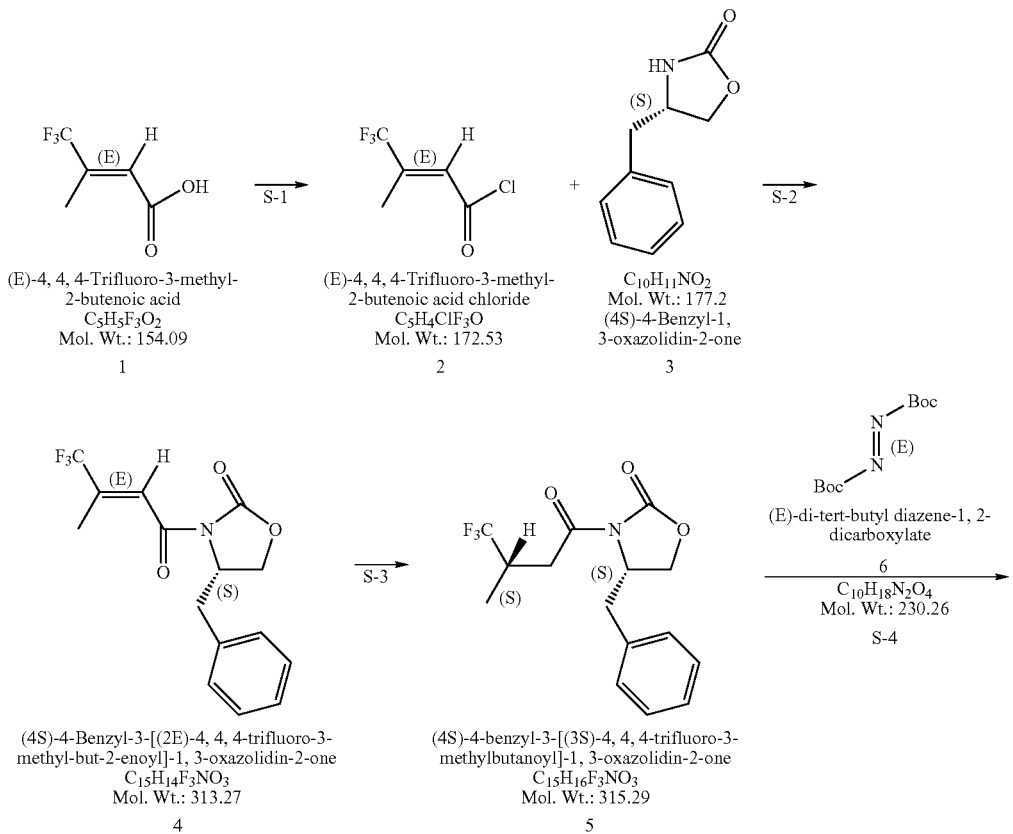

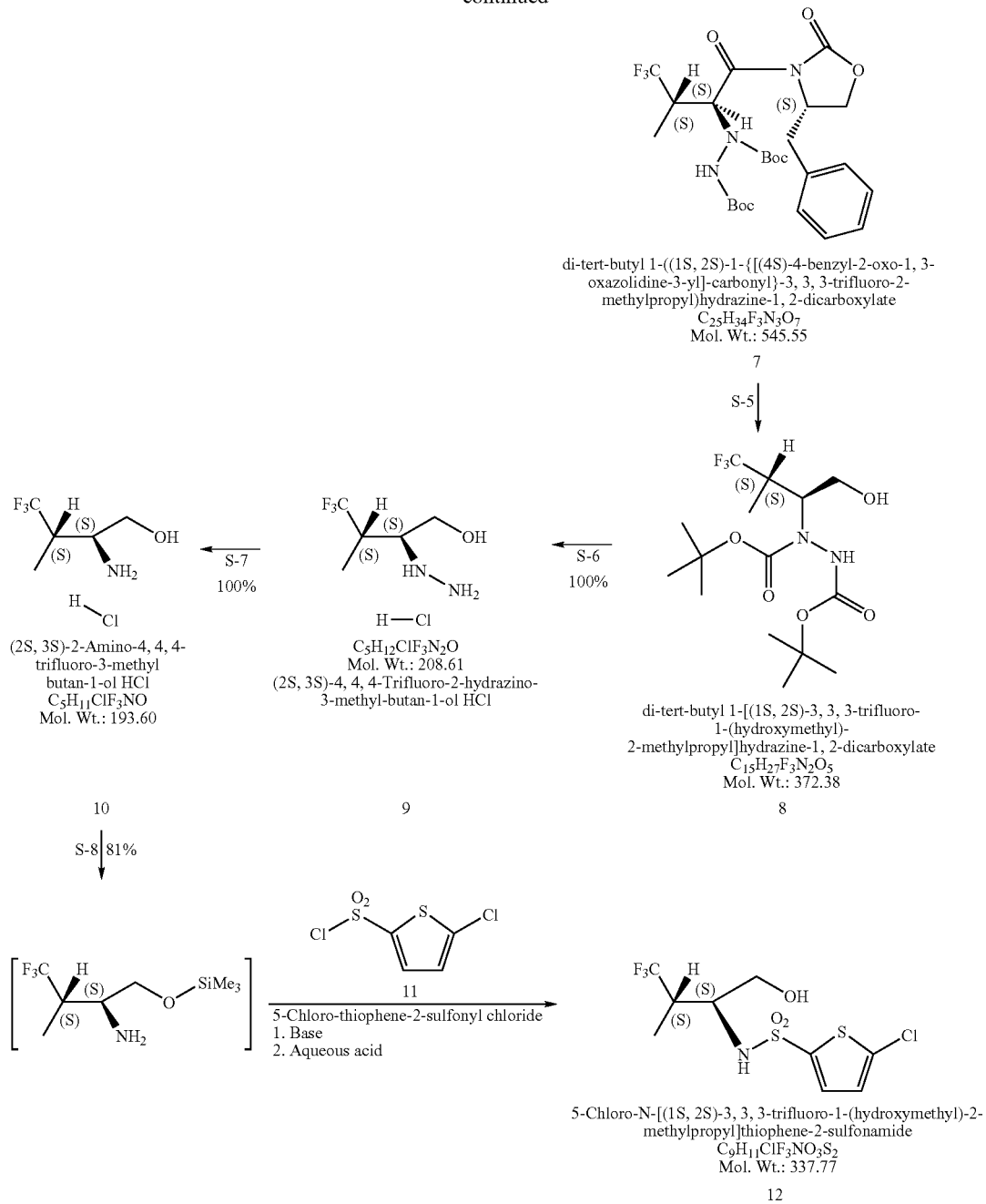

Example 2

Preparation of 5-Chloro-N-[(1S,2S)-3,3,3-trifluoro-1-(hydroxymethyl)-2-methylpropyl]thiophene-2-sulfonamide (2S,3S)-2-Amino-4,4,4-trifluoro-3-methyl-butan-1-ol HCl (10) (385.5 g, 1.99 moles) was stirred with 3.8 L CH$_2$Cl$_2$ and 1007 g (9.96 mole, 5 equivalents) 1-methylmorpholine was added with a wash of 200 mL CH$_2$Cl$_2$. At 20-30° C., Me$_3$SiCl (443 g, 4.08 mole, 2.05 equivalents) was over 15-30 minutes. The solution was stirred for 1 h at 20-30° C., then cooled to 15-20° C. 454 g (2.09 moles, 1.05 equivalents) of 5-chloro-thiophene-2-sulfonyl chloride was added over 10-15 minutes at 18 to 24° C. and washed with 190 mL CH$_2$Cl$_2$. The temperature rose to 31.5° C. over 30 minutes with the reactor in a bath at 30° C. The mixture was stirred for 16 hours and tested by HPLC to assure that excess (1-10%) 5-chloro-thiophene-2-sulfonyl chloride remains. 22 mL 1-methylpiperazine (0.199 mole, 0.1 equivalents) was added. The solvent was removed by distillation under vacuum at 90 mm Hg in a bath at 20-30° C. 3.65 L isopropyl acetate and 2 N H$_2$SO$_4$ (2 L) were added, the mixture was stirred for 20 minutes and the layers separated. The aqueous layer was back extracted with 0.5 L isopropyl acetate. 2 L 2 N H$_2$SO$_4$, 2 L 1/2 saturated NaHCO$_3$ and 2 L water were used as a wash. The layers were clarified by filtration through 0.2 μM filter. The isopropyl acetate was removed under vacuum (40 to <10 mm Hg) to dryness giving 675 g of crude 5-Chloro-N-[(1S,2S)-3,3,3-trifluoro-1-(hydroxymethyl)-2-methylpropyl]thiophene-2-sulfonamide. The product was recrystallized from 10 volumes of 1:4 EtOAc/Heptanes giving 499 g after drying at 55° C. for 16 hours. A second crop of 49 g may be obtained from the mother liquors for a total yield of 548 g, 81%.

All publications cited in this specification are incorporated herein by reference. While the invention has been described with reference to a particularly preferred embodiment, it will be appreciated that modifications can be made without departing from the spirit of the invention. Such modifications are intended to fall within the scope of the appended claims.

The invention claimed is:

1. A method of selectively preparing a chiral amino alcohol useful in preparation of an amine sulfonated or acylated with a residue containing an alkyl, substituted aryl or substituted heteroaryl group, said method comprising the steps of:
   (a) reacting di-tert-butyl azodicarboxylate with an anion derived from (4S)-4-benzyl-3-[(S)-trifluoromethyl-alkyl substituted alkanoyl]-1,3-oxazolidin-2-one to afford a di-tert-butyl 1-(1S,2S)-([(4S)-4-benzyl-2-oxo-1,3-oxazolidine-3-yl]-carbonyl}-trifluoromethyl-alkyl substituted alkyl)hydrazine-1,2-dicarboxylate;
   (b) reducing the di-tert-butyl 1-(1S,2S)-(1-{[(4S)-4-benzyl-2-oxo-1,3-oxazolidine-3-yl]-carbonyl}trifluoromethyl-alkyl substituted alkyl)hydrazine-1,2-dicarboxylate of (a) to yield di-tert-butyl 1-(1S,2S)-[trifluoromethyl-alkyl substituted alkyl]hydrazine-1-(hydroxymethyl)-1,2-dicarboxylate;
   (c) deblocking the product of (b) with an acid to yield the acid addition salt of (2S,3S)-trifluoro-hydrazino-methyl alkan-1-ol; and
   (d) hydrogenating the acid addition salt of (2S,3S)-trifluor-2-hydrazino-methyl alkan-1-ol in the presence of suitable metal catalyst to yield the amino alcohol (2S,3S)-2-Amino-trifluoro-methyl alkan-1-ol HCl.

2. The method according to claim 1, further comprising the step of triturating the product of (d) in a suitable solvent to remove trapped metal contaminants from the catalyst.

3. The method according to claim 1, wherein the reacting step (a) is performed under cold conditions.

4. The method according to claim 1, wherein the reacting step (a) further comprises reacting the (4S)-4-benzyl-3-[(S)-trifluoromethyl-alkyl substituted alkanoyl]-1,3-oxazolidin-2-one with lithium diisopropyl amide or potassium bis(trimethyl)silylamide in a suitable solvent system.

5. The method according to claim 4, wherein the solvent comprises tetrahydrofuran.

6. The method according to claim 4, wherein the reacting step (a) further comprises quenching the reaction with glacial acetic acid.

7. The method according to claim 1, wherein the reduction step (b) is performed by reaction of dissolved di-tert-butyl 1-(1S,2S)-(1-{[(4S)-4-benzyl-2-oxo-1,3-oxazolidine-3-yl]-carbonyl}-trifluoromethyl-alkyl substituted alkyl)hydrazine-1,2-dicarboxylate and LiBH$_4$ in tetrahydrofuran and water or t-butyl methyl ether and water.

8. The method according to claim 1, wherein the deblocking step (c) comprises mixing di-tert-butyl 1-(1S,2S)-[trifluoromethyl-alkyl substituted alkyl]hydrazine-1-(hydroxymethyl)-1,2-dicarboxylate and HCl.

9. The method according to claim 8, wherein concentrated HCl is added to the di-tert-butyl 1-(1S,2S)-[trifluoromethyl-alkyl substituted alkyl]hydrazine-1-(hydroxymethyl)-1,2-dicarboxylate at 30° C. to 50° C.

10. The method according to claim 1, wherein the catalyst in the hydrogenating step is selected from the group consisting of PtO$_2$, PdO$_2$, and RaNi.

11. The method according to claim 1, wherein the reacting step comprises:
   reacting di-tert-butyl azodicarboxylate with a the anion derived from (4S)-4-benzyl-3-[(3S)-4,4,4-trifluoro-3-methylbutanoyl]-1,3-oxazolidin-2-one to afford a di-tert-butyl 1-((1S,2S)-1-{[(4S)-4-benzyl-2-oxo-1,3-oxazolidine-3-yl]-carbonyl}-3,3,3-trifluoro-2-methylpropyl)hydrazine-1,2-dicarboxylate.

12. The method according to claim 11, wherein the reducing step comprises:
   reducing the di-tert-butyl 1-((1S,2S)-1-{[(4S)-4-benzyl-2-oxo-1,3-oxazolidine-3-yl]-carbonyl}-3,3,3-trifluoro-2-methylpropyl)hydrazine-1,2-dicarboxylate of (a) to yield di-tert-butyl 1-[(1S,2S)-3,3,3-trifluoro-1-(hydroxymethyl)-2-methylpropyl]hydrazine-1,2-dicarboxylate.

13. The method according to claim 1, wherein the deblocking step comprises deblocking the product of (b) with an acid to yield the acid addition salt of (2S,3S)-4,4,4-trifluoro-2-hydrazino-3-methyl-butan-1-ol.

14. The method according to claim 1, wherein the hydrogenating step comprises
   hydrogenating the acid addition salt of (2S,3S)-4,4,4-trifluoro-2-hydrazino-3-methyl-butan-1-ol in the presence of suitable metal catalyst to yield the amino alcohol (2S,3S)-2-Amino-4,4,4-trifluoro3-methyl-butan-1-ol HCl.

15. A method of selectively preparing a chiral 1S, 2S, aryl or heterocyclic sulfonamide, said method comprising the steps of:
   (a) reacting a di-tert-butyl diazene-1,2-dicarboxylate with a (4S)-4-benzyl-3-[(S)-trifluoromethyl-alkyl substituted alkanoyl]-1,3-oxazolidin-2-one to afford a di-tert-butyl 1-(1S,2S)-([(4S)-4-benzyl-2-oxo-1,3-oxazolidine-3-yl]-carbonyl}-trifluoromethyl-alkyl substituted alkyl)hydrazine-1,2-dicarboxylate;
   (b) reducing the di-tert-butyl 1-(1S,2S)-(1-{[(4S)-4-benzyl-2-oxo-1,3-oxazolidine-3-yl]-carbonyl}-trifluoromethyl-alkyl substituted alkyl)hydrazine-1,2-dicarboxylate of (a) to yield di-tert-butyl 1-(1S,2S)-[trifluoromethyl-alkyl substituted alkyl]hydrazine-1-(hydroxymethyl)-1,2-dicarboxylate;
   (c) deblocking the product of (b) with an acid to yield the acid addition salt of (2S,3S)-trifluoro-hydrazino-methyl alkan-1-ol;
   (d) hydrogenating the acid addition salt of (2S,3S)-trifluor-2-hydrazino-methyl alkan-1-ol in the presence of suitable metal catalyst to yield the amino alcohol (2S,3S)-2-Amino-trifluoro methyl alkan-1-ol HCl;
   (e) triturating the product of (d) in a suitable solvent to remove trapped metal contaminants from the catalyst; and
   (f) reacting the amino alcohol or salt thereof with a heterocyclic or aryl-substituted sulfonyl chloride.

16. The method according to claim 15 wherein the reacting step (e) further comprises mixing the amino alcohol or salt thereof with a suitable solvent and a tertiary base.

17. The method according to claim 15, wherein the method further comprises the steps of protecting the amino alcohol by silylation prior to reacting (f) and, following reacting (f), deblocking to yield 5-halo-N-[(1S,2S)-3,3,3-trifluoro-1-(hydroxymethyl)-2-methylpropyl]thiophene-2-sulfonamide.

18. The method according to claim 15, wherein the heterocyclic sulfonyl chloride is a 5-halo thiophene sulfonyl chloride.

19. The method according to claim 18 wherein the 5-halo-thiophene-sulfonyl chloride is 5-chloro-thiophene-2-sulfonyl chloride.

20. The method according to claim 19, wherein the 5-halo-thiophenesulfonyl chloride is dissolved in dichloromethane.

* * * * *